United States Patent
Stering

(10) Patent No.: US 9,810,564 B2
(45) Date of Patent: Nov. 7, 2017

(54) METHOD OF DETERMINING AN INTERNAL VOLUME OF A FILTER OR BAG DEVICE, COMPUTER PROGRAM PRODUCT AND A TESTING APPARATUS FOR PERFORMING THE METHOD

(71) Applicant: Sartorius Stedim Biotech GmbH, Goettingen (DE)

(72) Inventor: Magnus Andreas Stering, Le mesnil le roi (FR)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 292 days.

(21) Appl. No.: 14/644,331

(22) Filed: Mar. 11, 2015

(65) Prior Publication Data
US 2015/0300863 A1 Oct. 22, 2015

(30) Foreign Application Priority Data
Apr. 16, 2014 (EP) .................................. 14290111

(51) Int. Cl.
G01F 17/00 (2006.01)
G01N 7/00 (2006.01)

(52) U.S. Cl.
CPC .............. *G01F 17/00* (2013.01); *G01N 7/00* (2013.01)

(58) Field of Classification Search
CPC .................................. G01F 17/00; G01N 7/00
USPC ....................................................... 73/37, 149
See application file for complete search history.

(56) References Cited

U.S. PATENT DOCUMENTS

| 6,568,282 B1* | 5/2003 | Ganzi .................. B01D 65/102 73/38 |
| 7,252,014 B1 | 8/2007 | Mayer et al. |
| 2005/0247110 A1* | 11/2005 | Sagi .................... G01M 3/3254 73/40 |

(Continued)

FOREIGN PATENT DOCUMENTS

WO    2005/114116    12/2005

OTHER PUBLICATIONS

European Search Report dated Sep. 18, 2014.

*Primary Examiner* — R. A. Smith
*Assistant Examiner* — John M Royston
(74) *Attorney, Agent, or Firm* — Gerald E. Hespos; Michael J. Porco; Matthew T. Hespos

(57) ABSTRACT

A method of determining an internal volume (V) of a filter or bag device includes pressurizing the device to a first pressure ($p_1$) lower than a proof pressure by supplying a test gas, pressurizing the device to proof pressure ($p_p$), and at the same time, measuring the mass flow (m) or the volumetric flow of test gas, determining the gas temperature (T), and determining the internal volume (V) based on the equation for ideal gases, such that: $V = m \times R \times T / (p_p - p_1)$ where V is the internal volume, m is the mass flow, R is the gas constant, T is the gas temperature, $p_p$ is the proof pressure and $p_1$ is the first pressure. A computer program product and a testing apparatus for performing the above-mentioned method also are provided.

15 Claims, 5 Drawing Sheets

(56) References Cited

U.S. PATENT DOCUMENTS

2007/0289390 A1\* 12/2007 Ascheman ................ G01F 1/76
                                                       73/861
2011/0042298 A1\* 2/2011 Stouffer ............. B01D 39/2062
                                                       210/443
2012/0059603 A1     3/2012 Stering \* cited by examiner

METHOD OF DETERMINING AN INTERNAL VOLUME OF A FILTER OR BAG DEVICE, COMPUTER PROGRAM PRODUCT AND A TESTING APPARATUS FOR PERFORMING THE METHOD

BACKGROUND

1. Field of the Invention

The invention relates to a method of determining an internal volume of a filter or bag device, a computer program product and a testing apparatus for performing the method.

2. Description of the Related Art

According to the prior art, as e.g. disclosed in US 2012/0059603 A1, an integrity test is performed on a filter device on the basis of a pressure loss of a wetted hydrophilic or hydrophobic filter material of the filter device. Such an integrity test requires volume determination and therefore a long time to determine the integrity of the filter device.

Accordingly, it is the problem of the invention to provide an improved testing method and a corresponding testing apparatus that can shorten the time required for testing.

SUMMARY OF THE INVENTION

According to one aspect, the method for determining an internal volume of a filter or bag device comprises: pressurizing the device to a first pressure lower than a second or proof pressure by supplying a test gas. The first pressure is preferably higher than atmospheric pressure. The method then includes pressurizing the device to the second or proof pressure that is higher than the first pressure, and at the same time, measuring the mass flow or the volumetric flow of test gas required to increase the pressure within the device from the first to the second pressure. The method further includes determining the gas temperature (T), and determining the internal volume (V) based on the equation for ideal gases, such that: $V = m \times R \times T / (p_p - p_1)$, where V is the internal volume, m is the mass flow, R is the gas constant, T is the gas temperature, $p_p$ is the proof pressure and pi is the first pressure. As the internal volume is determined on the basis of a calculation of the equation of ideal gases, a time required for testing the filter or bag device is shortened remarkably.

The method may further comprise measuring a first gas temperature after pressurizing the device to the first pressure and before pressurizing the device to the proof pressure, measuring a second gas temperature after pressurizing the device to the second or proof pressure, and correcting the calculation of the internal volume by the gas temperature difference between the first gas temperature and the second gas temperature measured after pressurizing the device to the proof pressure.

The method may also comprise stabilizing the gas temperature after pressurizing the device to the first pressure. Stabilizing the gas temperature can improve preciseness of the testing method. Further, by setting the first pressure close to the proof pressure, an influence of a gas temperature change can be minimized.

A difference between the proof pressure and the first pressure may be in the range of between about 3 to about 20 kPa, preferably between about 6 and about 10 kPa, and/or the proof pressure may be in the range of between about 200 to about 500 kPa, preferably between about 300 and about 400 kPa.

The method may further comprise the step of determining a device failure when the determined internal volume exceeds a specified maximum value.

The method further may comprise the step of measuring a mass flow or a volumetric flow on the basis of a diffusion rate at the first pressure and at the proof pressure.

The method may further comprise the step of determining a device failure when the diffusion rate at the proof pressure divided by the diffusion rate at the first pressure exceeds a predetermined limit.

Nitrogen or helium may be the test gas.

The calculating step is performed by a microprocessor.

According to a further aspect, there is provided a computer program product comprising computer-readable instructions, which when loaded and executed on a suitable system, can perform the steps of the above-mentioned method.

According to a further aspect, there is provided a testing apparatus for performing the above-mentioned method. The testing device may comprise at least one pressure sensor for determining the first pressure and the proof pressure, a flow meter for determining a mass flow or a volumetric flow of the test gas, a test gas inlet connectable to a test gas supply, and a control device for determining the internal volume of a filter or bag device to be tested on the basis of at least the first pressure, the proof pressure and the mass flow or volumetric flow of test gas.

The testing apparatus may further comprise at least one temperature sensor for measuring the temperature of the device to be tested.

The testing apparatus may further comprise a proportional valve for supplying the test gas with a predetermined flow rate and/or pressure.

The testing apparatus may further comprise a vent valve for venting the device to be tested and/or a shut-off valve for shutting off a test gas supply.

The invention will be further explained by referring to an embodiment shown in the enclosed figures.

DETAILED DESCRIPTION OF THE PREFERRED EMBODIMENTS

Figure 1:
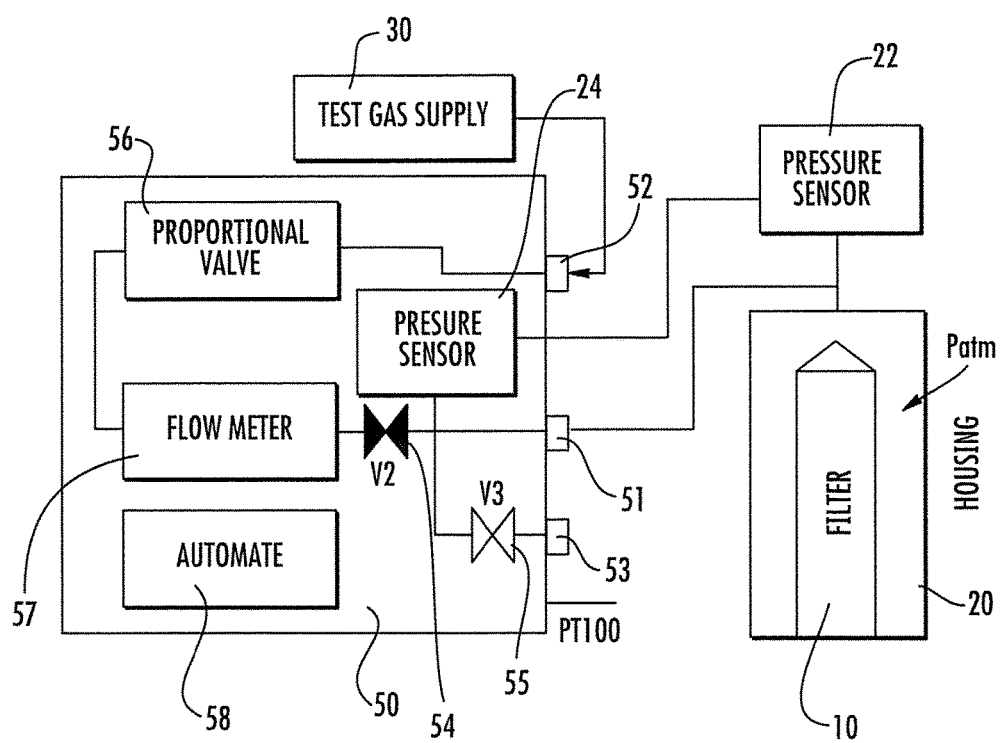
FIG. 1 shows a filter or bag device arranged in a test housing and connected to a testing apparatus.

As shown in FIG. 1, the filter or bag device 10 is arranged or mounted within a test housing 20 in a fluid tight manner. Before testing, atmospheric pressure Patm is within the test housing 20. The test housing 20 is connected to a testing apparatus 50 via a test gas outlet 51 of the testing apparatus 50. Further, a test gas supply 30, supplying a test gas such as nitrogen or helium is connected to a test gas inlet 52 of the testing apparatus 50.

An internal fluid line connects the test gas inlet 52 of the testing apparatus 50 with the test gas outlet 51 so as to supply the test gas from the test gas inlet 52 via the test gas outlet 51 to the test housing 20. Further, a flow meter 57 is arranged within the fluid line between the test gas inlet 52 and the test gas outlet 51 so as to determine or measure the mass flow and/or the volumetric flow rate of test gas through the fluid line.

Preferably, a shut-off valve 54 and/or a proportional valve 56 may also be arranged within the fluid line of the testing apparatus 50. The shut-off valve 54 may completely shut off the test gas supply to the test gas outlet 51. The proportional valve 56 may be used to control the flow rate or mass flow of test gas through the fluid line. Further preferred, a pressure sensor 24 is arranged within the fluid line so as to determine the pressure of the test gas.

Alternatively or additionally, a pressure sensor 22 may be connected to the test housing 20 so as to determine the pressure within the test housing 20.

Further, a calculating means (automate) 58 is arranged within the testing apparatus 50 so as to calculate an internal volume of the test housing 20 based on various parameters, such as the measured pressure measured by either of pressure sensor 22 and/or pressure sensor 24, a gas temperature T measured by a temperature sensor (not shown) arranged preferably within the test housing 20, and a mass flow or volumetric flow rate of test gas measured by the flow meter 57.

The gas temperature T can be measured directly by a temperature sensor or indirectly by measuring e.g. a temperature of the test housing 20 and estimating a temperature difference between the temperature of the test housing 20 and the gas temperature T.

Various temperature sensors may be applied such as a thermistor whose resistance varies significantly with temperature or an optoelectronic device.

Optoelectronic devices measure temperatures by means of optical fibres functioning as linear sensors. Temperatures are recorded along the optical sensor cable, thus not at points, but as a continuous profile. A high accuracy of temperature determination is achieved over great distances. Typically, the temperature can be located to a spatial resolution of 1 m with an accuracy to within ±1° K at a resolution of 0,01K.

Preferably, a vent valve 55 also is arranged or mounted within the testing apparatus 50 for venting the fluid line between the test gas inlet 52 and a test gas outlet 51 via a venting outlet 53. It should be mentioned, that venting the fluid line between the test gas inlet 52 and the test gas outlet 51 may also be applied to vent the test housing 20 being connected to the test gas outlet 51 of the testing apparatus 50.

Figure 2:
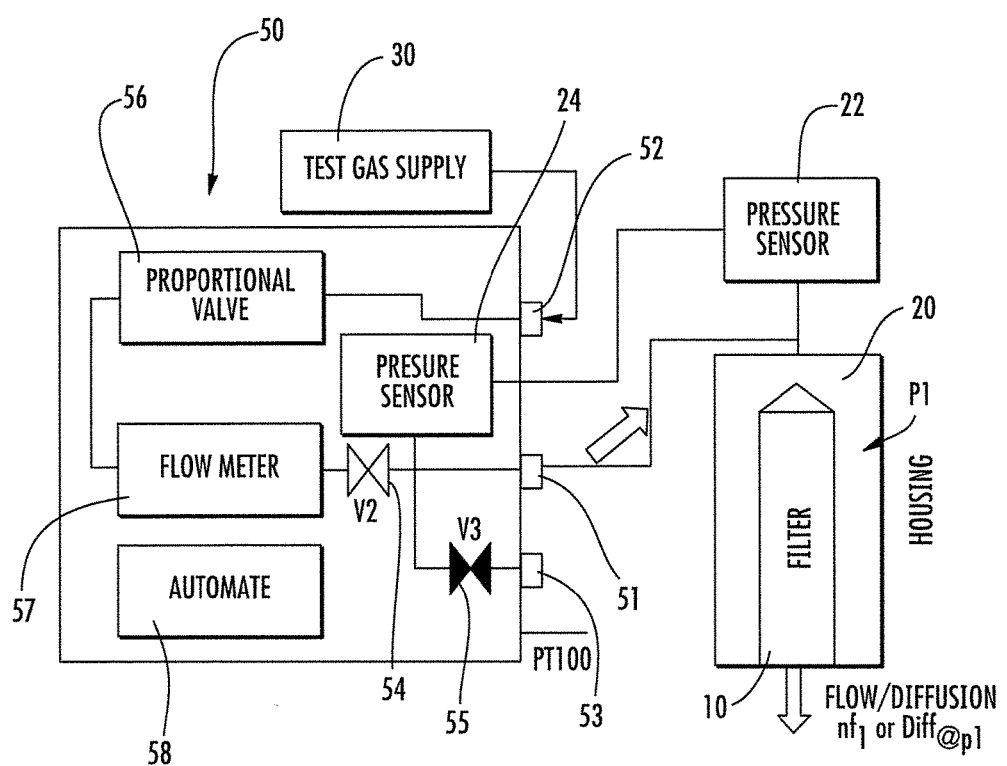
FIG. 2 shows the arrangement of FIG. 1, wherein a first pressure is applied to the test housing.
Figure 3:
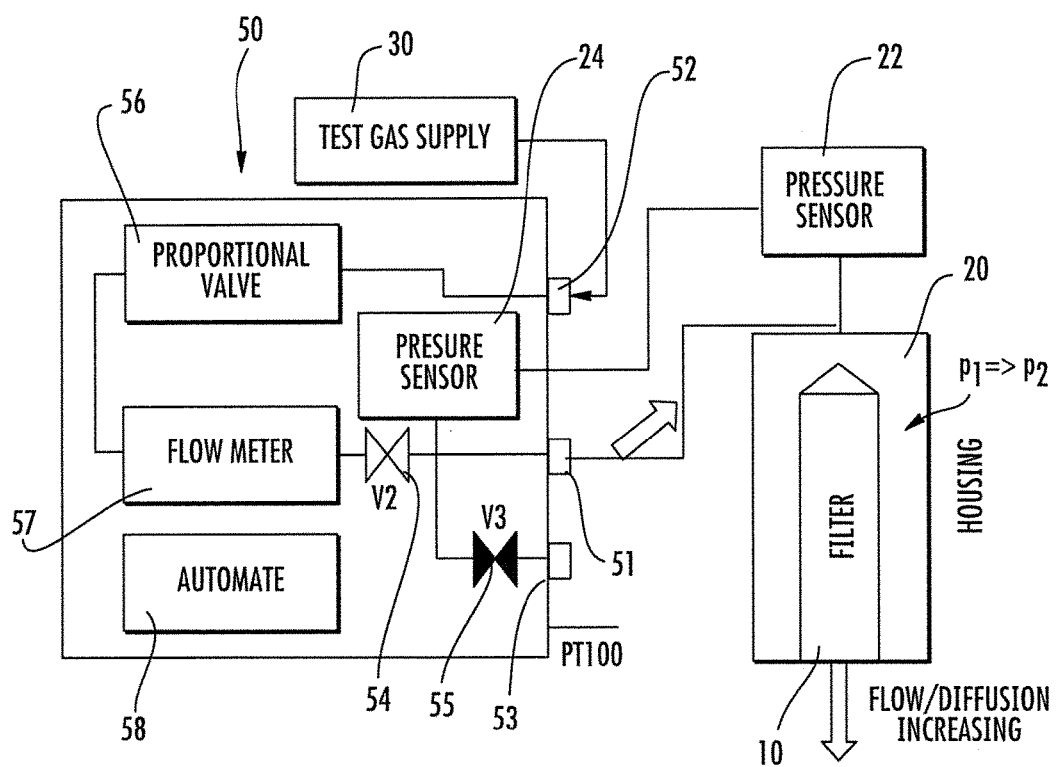
FIG. 3 shows the arrangement of FIG. 1 wherein the pressure within the test housing is increased from the first pressure to proof pressure.

The testing method will now be explained with reference to FIGS. 2 to 5. In a first step, test gas is supplied by the test gas supply 30 via the testing apparatus 50 to the test housing 20 until a first pressure p1 is achieved, as shown in FIG. 2. In this condition, when the first pressure p1 is within the test housing 20, a flow or diffusion rate nf1 escapes from the filter 10 to the outlet, as shown by the arrow in FIG. 2.

Preferably, a first gas temperature T1 is measured after achieving the first pressure p1 within the test housing 20. Further preferred, the first gas temperature T1 is measured after the elapse of a certain time so as to stabilize the gas temperature within the test housing 20.

In a second step, the first pressure p1 within the test housing 20 is increased so as to achieve a second or proof pressure pp or p2. It should be clear, that the flow or diffusion rate increases by increasing the pressure within the test housing 20, as shown by the arrow in FIG. 3.

Figure 4:
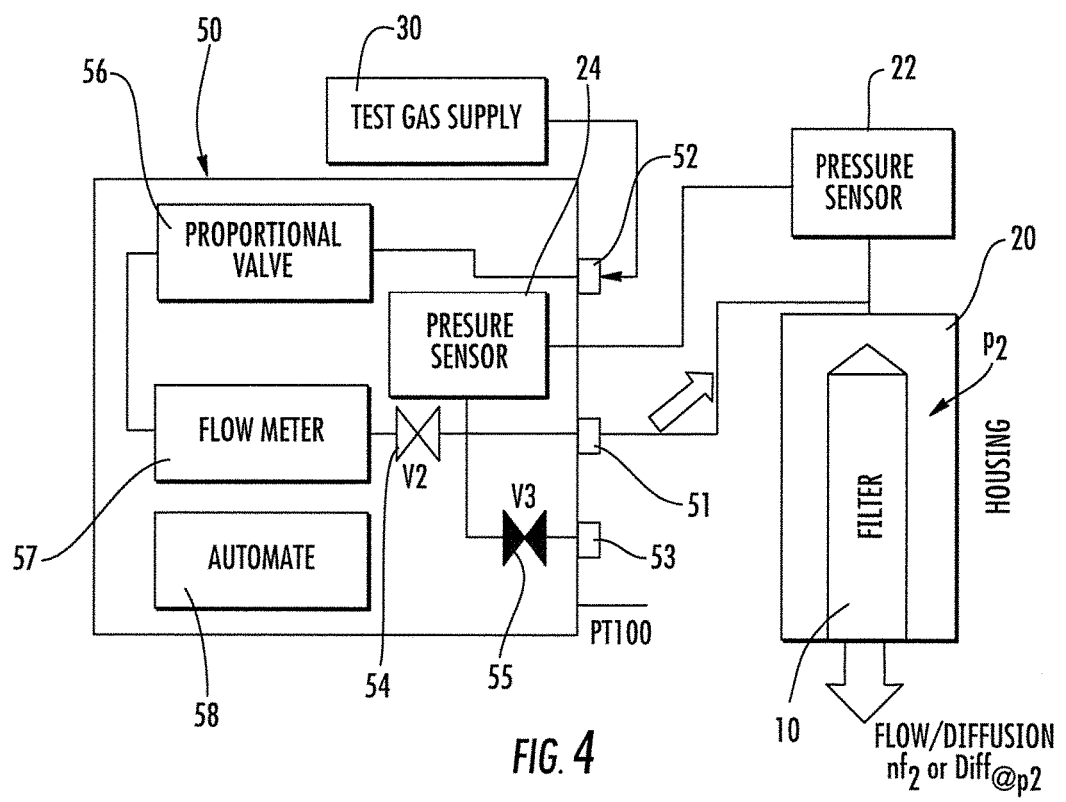
FIG. 4 shows the arrangement of FIG. 1, wherein the proof pressure is set within the test housing.

In a third step, the second or proof pressure p2 or pp is achieved within the test housing 20, as shown in FIG. 4. In this condition, the flow or diffusion rate nf2 escaping from the test housing 20 via the filter device 10 is established. It should be clear that the flow or diffusion rate nf2 is higher than the flow or diffusion rate nf1 established with the first pressure p1 which is lower than the second or proof pressure p2 or pp.

Preferably, the gas temperature within the test housing 20 is measured after achieving the second or proof pressure p2 or pp. Further preferred, the elapse of a certain time is waited until measuring the gas temperature within the test housing 20, so as to stabilize the temperature.

In a fourth step, the calculating means 58 calculates the internal volume of the test housing 20 containing the filter or bag device 10 to be tested. This calculation is performed by the equation for ideal gases:

$$V = m \times R \times T / (p_p - p_1)$$

In this equation V is the internal volume of the test housing 20 containing the filter or bag device 10 to be tested, m is the mass flow of test gas, R is the gas constant, T is the gas temperature in Kelvin, $p_p$ is the proof pressure and $p_1$ is the first pressure.

In a fifth step, the calculated internal volume V is compared with a predetermined maximum and/or minimum value. In case the determined internal volume V is outside the predetermined volume range, the filter or bag device 10 is determined to be faulty. In contrast, should the internal volume V be within the predetermined volume range, the filter or bag device 10 is determined to fulfill the requirements, e.g. the required integrity.

Further preferred, the flow or diffusion rate $nf_1$ with the first pressure $p_1$ applied to the test housing 20 is compared to the flow or diffusion rate $nf_2$ with the second or proof pressure $p_p$ applied to the test housing 20. Normally, the flow or diffusion rate should increase linearly with an increased pressure applied to the test housing 20. In case of a faulty filter or bag device 10, however, the flow or diffusion rate increases over-linearly. Therefore, a comparison between the flow diffusion rate $nf_2$ with the second or proof pressure applied with the flow or diffusion rate $nf_1$ with the first pressure applied can also be used to determine whether the filter or bag device 10 fulfils the specified requirements, i.e. integrity of the filter or bag device 10.

Figure 5:
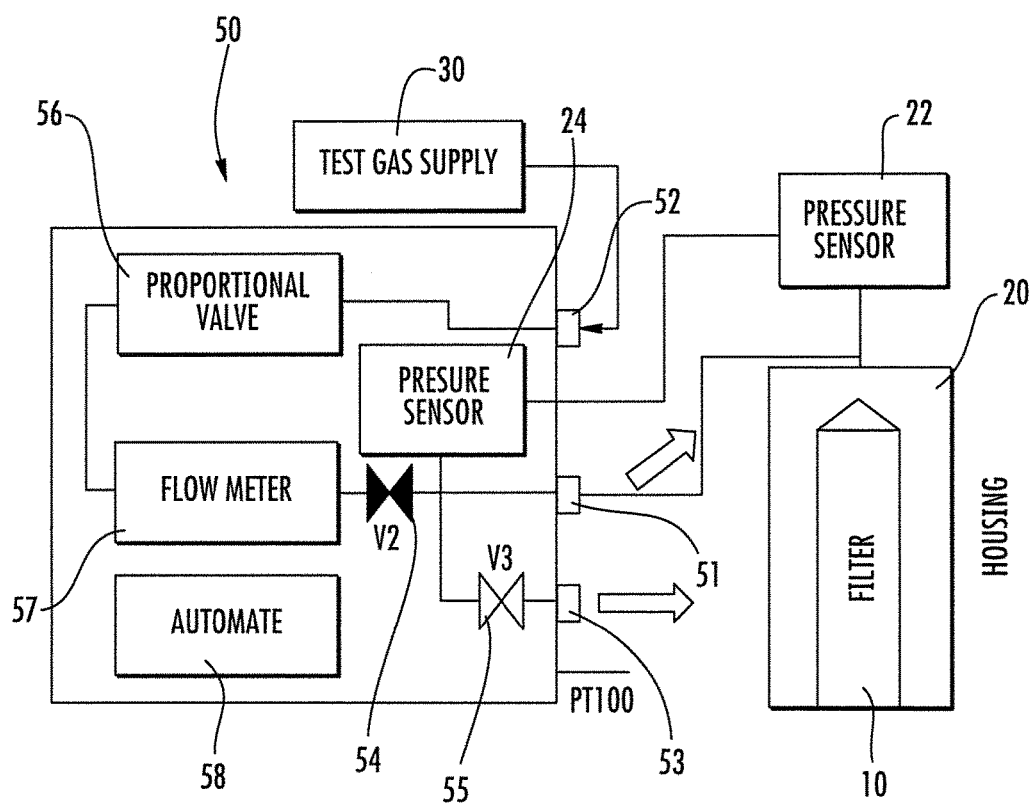
FIG. 5 shows the arrangement of FIG. 1, wherein the pressure within the test housing is vented into the atmosphere.

A sixth step is shown in FIG. 5 in which the filter housing 20 is vented by closing the shut-off valve 54 of the testing apparatus 50 and opening the vent valve 55 so as to vent the test gas within the test housing 20 via the venting outlet 53 of the testing apparatus 50. Decreasing the pressure within the test housing 20 to substantially atmospheric pressure enables the test housing 20 to be opened so as to remove the filter or bag device 10.

Preferably, nitrogen or helium or air is used as the test gas. However, any adequate test gas can be used which substantially fulfils the requirements of an ideal gas and does not contaminate the filter or bag device 10 to be tested.

The calculating means comprises preferably a central processing unit CPU, a storage device, a random access memory RAM and a read only memory ROM etc. Although not shown, an input device and a display unit may also be provided to the testing apparatus 50 so as to input various data by an operator and display the test result by means of the display unit (not shown).

Preferably, the filter or bag device 10 may be wetted before performing the volume test. A bubble point test or a multipoint diffusion test may also be performed by the described testing apparatus 50. Instead of using nitrogen or helium, air may also be used so as to reduce the test gas costs. Although not shown, the test housing 20 may be provided with a liquid supply at the bottom thereof so as to wet a membrane of the filter or bag device 10. Further, a vent valve and a vent port (not shown) may also be provided at the test housing 20.

List of Reference Numerals 10 filter or bag device
20 test housing
22 external pressure sensor
24 internal pressure sensor
30 test gas supply
50 testing apparatus
51 test gas outlet
52 test gas inlet
53 venting outlet
54 shut-off valve
55 vent valve
56 proportional valve
57 flow meter
58 calculating means (automate)

What is claimed is:

1. A method of determining an internal volume (V) of a filter or bag device (10) comprising:
   pressurizing the device to a first pressure ($p_1$) lower than a proof pressure by supplying a test gas,
   pressurizing the device to the proof pressure ($p_p$), and at the same time, measuring the mass flow (m) of test gas,
   determining the gas temperature (T), and
   determining the internal volume (V) based on the equation for ideal gases, such that:

$$V = m \times R \times T / (p_p - p_1)$$

wherein V is the internal volume, m is the mass flow, R is the gas constant, T is the gas temperature, $p_p$ is the proof pressure and $p_1$ is the first pressure.

2. The method of claim 1, further comprising:
   measuring a first gas temperature ($T_1$) after pressurizing the device to the first pressure ($p_1$) and before pressurizing the device to the proof pressure ($p_p$),
   measuring a second gas temperature after pressurizing the device to the proof pressure, and
   correcting the calculation of the internal volume (V) by the temperature difference between the first gas temperature ($T_1$) and the gas temperature (T) measured after pressurizing the device to the proof pressure ($p_p$).

3. The method of claim 1, further comprising stabilizing the temperature after pressurizing the device to the first pressure ($p_1$).

4. The method of claim 1, wherein a difference between the proof pressure ($p_p$) and the first pressure ($p_1$) is in a range of between about 3 to about 400 kPa, depending on the filter type to be tested, and/or the proof pressure ($p_p$) is in a range of between about 70 to about 500 kPa, depending on the filter type to be tested.

5. The method of claim 1, further comprising determining a device failure when the determined internal volume (V) falls outside a specified volume range.

6. The method of claim 1, further comprising measuring a mass flow on the basis of a diffusion rate (nf) at the first pressure ($p_1$) and at the proof pressure ($p_p$).

7. The method of claim 6, further comprising determining a device failure when the diffusion rate ($nf_2$) at the proof pressure ($p_p$) divided by the diffusion rate ($nf_1$) at the first pressure ($p_1$) exceeds a predetermined limit.

8. The method of claim 1, wherein nitrogen or helium or air is used as the test gas.

9. The method of claim 1, wherein the step of determining the internal volume (V) is performed by a microprocessor.

10. A computer program product comprising: non-transitory computer-readable instructions, which when loaded and executed on a suitable system, is configured to perform the steps of:
    pressurizing a filter or bag device to a first pressure ($p_1$) lower than a proof pressure by supplying a test gas,
    pressurizing said device to the proof pressure ($p_p$), and at the same time, measuring the mass flow (m) of test gas,
    determining the gas temperature (T), and
    determining the internal volume (V) based on the equation for ideal gases, such that:

$$V = m \times R \times T / (p_o - p_1)$$

wherein V is the internal volume, m is the mass flow, R is the gas constant, T is the gas temperature, $p_p$ is the proof pressure and $p_1$ is the first pressure.

11. A testing apparatus for determining an internal volume (V) of a filter or bag device (10), the testing device comprising:
    a test gas inlet (52) connectable to a test gas supply (30),
    a test gas outlet (51) in gas communication with the test gas inlet (52) for supplying the test gas to the internal volume (V) of the filter or bag device (10),
    a flow meter (57) in communication with the test gas inlet (52) and the test gas outlet (51) for determining a mass flow (m) of the test gas,
    at least one pressure sensor (22, 24) for determining a first pressure ($p_1$) and a proof pressure ($p_o$) that is higher than the first pressure ($p_1$), and
    a control device for determining the internal volume (V) of a filter or bag device (10) to be tested on the basis of at least the first pressure, the proof pressure and the mass flow or volumetric flow of test gas based on the equation for ideal gases, such that:

$$V = m \times R \times T / (p_p - p_1)$$

wherein R is the gas constant and T is the gas temperature.

12. The testing apparatus of claim 11, further comprising at least one temperature sensor for measuring the temperature (T) of the device to be tested.

13. The testing apparatus of claim 11, further comprising a proportional valve (56) for supplying the test gas at a predetermined flow rate and/or pressure.

14. The testing apparatus of claim 11, further comprising a vent valve (V3) for venting the device to be tested and/or a shut-off valve (V2) for shutting off the supply of test gas.

15. The testing apparatus of claim 11, further comprising a supply of nitrogen and/or helium and/or air.

* * * * *